(12) United States Patent
Park

(10) Patent No.: US 9,131,854 B2
(45) Date of Patent: Sep. 15, 2015

(54) APPARATUS AND METHOD OF MEASURING BLOOD PRESSURE OF EXAMINEE WHILE DETECTING BODY ACTIVITY OF EXAMINEE

(75) Inventor: Won-Hee Park, Gyeongsan-si (KR)

(73) Assignee: JAWON MEDICAL CO., LTD, Gyeongsan-si (KR)

( * ) Notice: Subject to any disclaimer, the term of this patent is extended or adjusted under 35 U.S.C. 154(b) by 523 days.

(21) Appl. No.: 13/390,729

(22) PCT Filed: Jun. 18, 2010

(86) PCT No.: PCT/KR2010/003974
§ 371 (c)(1),
(2), (4) Date: Mar. 20, 2012

(87) PCT Pub. No.: WO2011/025134
PCT Pub. Date: Mar. 3, 2011

(65) Prior Publication Data
US 2012/0172733 A1 Jul. 5, 2012

(30) Foreign Application Priority Data

Aug. 27, 2009 (KR) .......................... 10-2009-0079647
Apr. 26, 2010 (KR) .......................... 10-2010-0038341

(51) Int. Cl.
*A61B 5/02* (2006.01)
*A61B 5/0205* (2006.01)
*A61B 5/021* (2006.01)
*A61B 5/103* (2006.01)
*A61B 5/11* (2006.01)

(52) U.S. Cl.
CPC ........... *A61B 5/0205* (2013.01); *A61B 5/02141* (2013.01); *A61B 5/021* (2013.01); *A61B 5/103* (2013.01); *A61B 5/1118* (2013.01)

(58) Field of Classification Search
USPC .................................................. 600/485–507
See application file for complete search history.

(56) References Cited

U.S. PATENT DOCUMENTS

| 8,233,969 | B2* | 7/2012 | Muhlsteff et al. | 600/509 |
| 8,727,999 | B2* | 5/2014 | Kim et al. | 600/500 |
| 2005/0033188 | A1* | 2/2005 | Whitaker et al. | 600/490 |
| 2006/0155196 | A1* | 7/2006 | Ramsey | 600/490 |
| 2007/0032730 | A1* | 2/2007 | Hung | 600/490 |

(Continued)

FOREIGN PATENT DOCUMENTS

| KR | 1994-007154 U | 4/1994 |
| KR | 1999-0065818 A | 8/1999 |
| KR | 10-2006-0085158 A | 7/2006 |

*Primary Examiner* — Jacqueline Cheng
*Assistant Examiner* — Eric Messersmith
(74) *Attorney, Agent, or Firm* — Birch, Stewart, Kolasch & Birch, LLP

(57) ABSTRACT

An apparatus and a method of measuring a blood pressure of an examinee while detecting the body activity of the examinee uses a pressurizing unit of a blood pressure gauge having first and second driving modes for pressurizing a cuff. A central processing unit classifies signals, which represent the movement, the position, or the direction of the blood pressure gauge detected by a sensor installed in a body of the blood pressure gauge, into a plurality of groups, and selectively performs the first driving mode or the second driving mode according to signal bands classified into the groups. The central processing unit is configured to generate blood pressure data so that the variation in the blood pressure of the examine is exactly determined according to the activity degree and the posture of the examinee.

7 Claims, 6 Drawing Sheets

(56) References Cited

U.S. PATENT DOCUMENTS

| | | | |
|---|---|---|---|
| 2008/0183082 A1* | 7/2008 | Farringdon et al. | 600/481 |
| 2009/0018402 A1* | 1/2009 | Suda | 600/300 |
| 2009/0018404 A1* | 1/2009 | Fendelander et al. | 600/301 |
| 2009/0069642 A1* | 3/2009 | Gao et al. | 600/300 |
| 2009/0076343 A1* | 3/2009 | James et al. | 600/301 |
| 2009/0076346 A1* | 3/2009 | James et al. | 600/301 |
| 2009/0076349 A1* | 3/2009 | Libbus et al. | 600/301 |
| 2009/0076350 A1* | 3/2009 | Bly et al. | 600/301 |
| 2009/0105607 A1* | 4/2009 | Shahrestani et al. | 600/559 |
| 2009/0156946 A1* | 6/2009 | Lane et al. | 600/490 |

* cited by examiner

FIG 1 measured blood pressure systolic blood pressure : 130mmHg, distolic blood pressure : 70mmHg, pulse rate 76

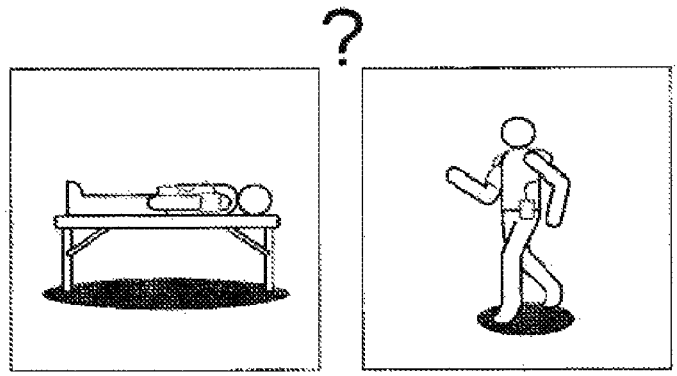

It is not determined if the blood pressure is measured
when an examinee lies down or stands up.

FIG 2 measured blood pressure systolic blood pressure : 130mmHg, distolic blood pressure : 70mmHg, pulse rate 76

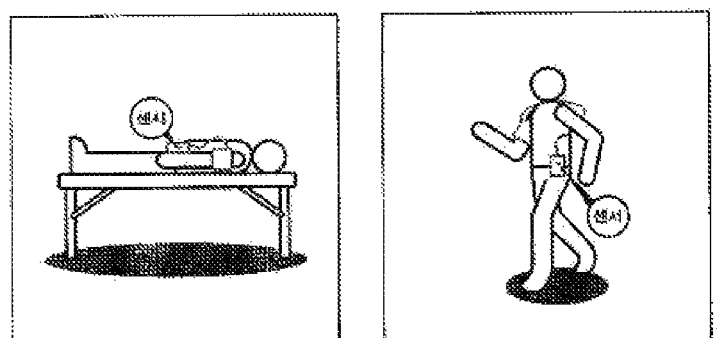

It is not determined if the blood pressure is measured
when an examinee lies down or stands up.

| | MEASUREMENT DATE | SYSTOLIC | DIASTOLIC | PULSE |
|---|---|---|---|---|
| 4 | 2009-11-09 10:30:00 | 127 | 76 | 60 |
| 5 | 2009-11-09 10:45:00 | 124 | 92 | 61 |
| 6 | 2009-11-09 11:00:00 | 142 | 77 | 71 |
| 7 | 2009-11-09 11:15:00 | 161 | 107 | 76 |
| 8 | 2009-11-09 11:45:00 | 127 | 84 | 68 |
| 9 | 2009-11-09 12:00:00 | 127 | 80 | 74 |
| 10 | 2009-11-09 12:15:00 | 148 | 84 | 73 |
| 11 | 2009-11-09 12:30:00 | 138 | 81 | 61 |
| 12 | 2009-11-09 12:45:00 | 127 | 75 | 61 |
| 14 | 2009-11-09 13:00:00 | 135 | 89 | 78 |
| 14 | 2009-11-09 13:30:00 | 160 | 101 | 66 |
| 15 | 2009-11-09 13:45:00 | 157 | 104 | 67 |
| 16 | 2009-11-09 14:00:00 | 166 | 107 | 66 |
| 17 | 2009-11-09 14:15:00 | 123 | 78 | 63 |

Blood Pressure: SYSTOLIC 166, DIASTOLIC 107, PULSE 66, MAP 127, PP 59. State: Fast walk.

FIG 8

| | MEASUREMENT DATE | SYSTOLIC | DIASTOLIC | PULSE |
|---|---|---|---|---|
| 29 | 2009-11-09 17:30:00 | 129 | 87 | 74 |
| 30 | 2009-11-09 17:45:00 | 126 | 83 | 75 |
| 31 | 2009-11-09 18:00:00 | 124 | 86 | 64 |
| 32 | 2009-11-09 18:15:00 | 125 | 91 | 76 |
| 33 | 2009-11-09 18:30:00 | 150 | 92 | 73 |
| 34 | 2009-11-09 18:45:00 | 142 | 100 | 72 |
| 35 | 2009-11-09 19:15:00 | 117 | 80 | 67 |
| 36 | 2009-11-09 19:30:00 | 132 | 77 | 73 |
| 37 | 2009-11-09 19:45:00 | 143 | 78 | 66 |
| 38 | 2009-11-09 20:00:00 | 168 | 104 | 76 |
| 39 | 2009-11-09 21:00:00 | 172 | 97 | 75 |
| 40 | 2009-11-09 21:15:00 | 168 | 113 | 63 |
| 41 | 2009-11-09 21:30:00 | 177 | 106 | 66 |
| 42 | 2009-11-09 21:45:00 | 144 | 91 | 76 |

Blood Pressure: SYSTOLIC 177, DIASTOLIC 106, PULSE 66, MAP 130, PP 71. State: Run.

APPARATUS AND METHOD OF MEASURING BLOOD PRESSURE OF EXAMINEE WHILE DETECTING BODY ACTIVITY OF EXAMINEE

TECHNICAL FIELD

The present invention relates to an apparatus and a method of measuring a blood pressure of an examinee while detecting the posture or the activity of the examinee. More particularly, the present invention relates to a blood pressure measurement system, which includes a sensor to detect the posture or the activity of an examinee such that the variation in the blood pressure of the examinee can be exactly detected according to the activity and postures of the examinee, and when the blood pressure of the examinee frequently varying in daily life is measured for 24 hours, the sensor detects activities such as sitting, standing, lying, walking, running, stair-stepping, and tossing and turning in sleeping and stores the information about the activities together with the measured blood pressure, so that the posture and the activity of the examinee can be determined as the blood pressure of the examinee is measured, thereby exactly diagnosing the variation in the blood pressure of the examinee.

BACKGROUND ART

A blood pressure gauge has been extensively used to monitor the blood pressure of an examinee, which frequently varies in daily life, for 24 hours and to measure the blood pressure of the examinee. Such a blood pressure gauge is a system used to measure the blood pressure of the examinee, which varies every moment, and to record measured blood pressure according to measurement time intervals of the blood pressure so that an expert can analyze the recorded results. However, the expert cannot exactly understand whether the variation of the blood pressure is derived from the variation in the posture of the examinee or the activity of the examinee, or derived from the individual peculiarities of the examinee. In addition, the expert cannot find the variation degree of blood pressure according to the degree of the activities such as exercising or walking.

In detail, as shown in FIG. 1, although measurement results such as the systolic pressure of 130 mmHg, the diastolic pressure of 70 mmHg, and a pulse rate of 76 are acquired through the conventional blood pressure gauge without a sensor to detect the posture or activity of the examinee, the expert does not determine if the measurement results are acquired when the examinee lies down or when the examinee is walking. In other words, since the expert examines the measurement results based on the estimate results for the bedtime, rising time, or activity time of the examinee according to the measurement time interval of the blood pressure, the expert cannot acquire information about the exact blood pressure of the examinee.

In addition, in order to measure the activity degree of the examinee, a passometer equipped with an accelerometer is used to detect the stepping degree of the examinee. However, actually, since the measurement of the activity information of the examinee acquired from an activity measuring unit or the passometer is performed separately from the measurement of the blood pressure of the examinee, the information about the blood pressure of a human body varying according to time intervals based on the activity information cannot be exactly acquired.

In addition, the blood pressure of the examinee may be changed due to the variation in the postures or the activity states of the examinee when the examinee stands up, sits down, lies down, runs, goes up the stairs, exercises, or takes a rest in daily life for 24 hours, or due to the degradation of the body function of the examinee.

Therefore, if the causes of the variation in the blood pressure of the examinee are exactly found, the accuracy of the measurement results of the blood pressure can be improved. In addition, if the fluctuating blood pressure of the examinee is measured when the examinee is exercising, for example, walking, running, or stair-stepping, the exact information about the blood pressure according to body conditions of the examinee can be acquired.

The information about a blood pressure, in which the body conditions of the examinee are exactly reflected, greatly contributes to the blood pressure diagnosis of the expert. However, since the postures or the activity state of the examinee cannot be detected, the blood pressure diagnosis is performed only based on the survey or explanation of the examinee and the estimation of the expert in a state in which the information about the postures or the activity state of the examinee is not reflected.

DISCLOSURE

Technical Problem

Accordingly, the present invention has been made to solve the above-mentioned problems occurring in the prior art, and an object of the present invention is to provide a blood pressure gauge and a method of measuring a blood pressure, capable of constructing a blood pressure measuring system to output the results of a blood pressure measured based on the body activity state of an examinee, so that the reliability for blood pressure measurement can be improved, and the information about the blood pressure of the examinee can be exactly determined.

Another object of the present invention is to provide a blood pressure gauge capable of displaying measurement values of the blood pressure of an examinee together with the activity state (e.g., sitting, lying, standing, walking, or exercising) of the examinee, and particularly preventing a cuff from being rapidly pressurized by driving the cuff at a second driving mode (sleep driving mode) instead of a first driving mode (normal driving mode) when the examinee lies down or is in a sleeping state, so that the examinee in the sleeping state is neither awake nor puts on the cuff without feeling repulsion for the cuff.

Technical Solution

An apparatus of measuring a blood pressure of an examinee while detecting a body activity of the examinee includes a cuff, a pressurizing unit to pressurize the cuff, a discharge unit to release a pressure of the cuff, a blood pressure measuring unit to measure the blood pressure by pressurizing the cuff, a central processing unit to perform a predetermined operation with respect to the measured blood pressure, a memory to store information about the blood pressure that is obtained from the operation, and a data output unit to output the information about the blood pressure stored in the central processing unit or the memory.

Particularly, a sensor is installed in a body of a blood pressure gauge to detect movement, a position, or a direction of the blood pressure gauge, and the central processing unit is configured to generate blood pressure data by performing the operation based on time to measure the blood pressure using the blood pressure measuring unit and a detected signal band of the sensor received corresponding to the time to measure the blood pressure.

The pressurizing unit has first and second driving modes for pressurizing the cuff, and the central processing unit classifies signals, which represent the movement, the position, or the direction of the blood pressure gauge detected by the sensor, into a plurality of groups, and selectively performs the first driving mode or the second driving mode according to signal bands classified into the groups.

The cuff is pressurized more rapidly at the first driving mode than at the second driving mode, and the central process unit performs the second driving mode if the blood pressure is measured in two signal bands selected from the grouped signal bands, and performs the first driving mode if the blood pressure is measured in remaining signal bands.

A method of measuring a blood pressure of an examinee while detecting a body activity of the examinee includes measuring a first blood pressure of the examinee by pressurizing a cuff with one of first and second driving modes of a pressurizing unit, receiving information about movement, a position, or a direction of a blood pressure gauge, which is detected by a sensor installed in a body of the blood pressure gauge, in real time and classifying signal bands of the information into a plurality of groups by a central processing unit, comparing the groups of the signal bands corresponding to a time interval, at which the first blood pressure of the examinee is measured, with each other and simultaneously outputting information about the movement, the position, or the direction of the blood pressure gauge and information about the measured blood pressure through an output unit, or storing the information about the movement, the position, or the direction of the blood pressure gauge and the information about the measured blood pressure in a memory by the central processing unit, measuring a second blood pressure of the examinee by selectively driving the first driving mode or the second driving mode according to positions corresponding to the grouped signal bands by the central processing unit, and repeating the information receiving, the group comparing, and the second blood pressure measuring for a predetermined period of time.

The cuff is pressurized more rapidly at the first driving mode than at the second driving mode, and the second driving mode is performed if the blood pressure is measured in two signal bands selected from the grouped signal bands, and the first driving mode is performed if the blood pressure is measured in remaining signal bands.

Advantageous Effects

As described above, the apparatus of measuring the blood pressure according to the present invention can check the variation of the blood pressure of the examinee according to the varying posture and the activity state of the examinee in real time, can exactly measure the blood pressure of the examinee even when the examinee tosses and turns in a sleeping state, and detect the variation of the blood pressure of the examinee according to the posture state or the degree of activities such as walking, running, stair stepping, standing, sitting, and lying in daily life, such that the variation of the examinee can be exactly monitored.

In addition, even when the examinee is in the sleeping, the examinee is prevented from being awaken or feeling repulsion due to vibration or noise caused by the sudden increase of pressure of the pressurizing unit. Accordingly, the examinee can feel stability and reliability with respect to the wearing of the cuff.

In addition, the sensor is provided in the body of the blood pressure gauge to detect the posture or the activity of the examinee, and an central process unit performs a comparison operation based on the information about the blood pressure of the examinee measured by a blood pressure measuring unit and the information about the posture or the activity detected in the same time interval as that of the blood pressure measurement, stores the information about the blood pressure of the examinee and the information about the posture or the activity of the examinee in the memory, and controls the output unit to output the information about the blood pressure of the examinee and the information about the posture or the activity of the examinee such that the information can be examined, simultaneously. Therefore, exact information can be provided so that the exact diagnosis of the variation in the blood pressure of the examinee can be performed.

DESCRIPTION OF DRAWINGS

FIG. 1 is a view showing an example of measuring a blood pressure by using an apparatus of measuring a blood pressure according to the related art;

FIG. 2 is a view showing an example of measuring a blood pressure by using an apparatus of measuring a blood pressure according to the present invention;

FIG. 5 is a view showing output data related to the blood pressure of an examinee measured by using the apparatus of measuring a blood pressure according to the present invention when the examinee stands up;

FIG. 6 is a view showing output data related to the blood pressure of the examinee measured by using the apparatus of measuring a blood pressure according to the present invention when the examinee is walking;

FIG. 7 is a view showing output data related to the blood pressure of the examinee measured by using the apparatus of measuring a blood pressure according to the present invention when the examinee is fast walking;

FIG. 8 is a view showing output data related to the blood pressure of the examinee measured by using the apparatus of measuring a blood pressure according to the present invention when the examinee is running;

BEST MODE

Mode for Invention

Hereinafter, the technical configuration and operation of an apparatus 100 of measuring a blood pressure according to the present invention will be described in detail.

Figure 3:
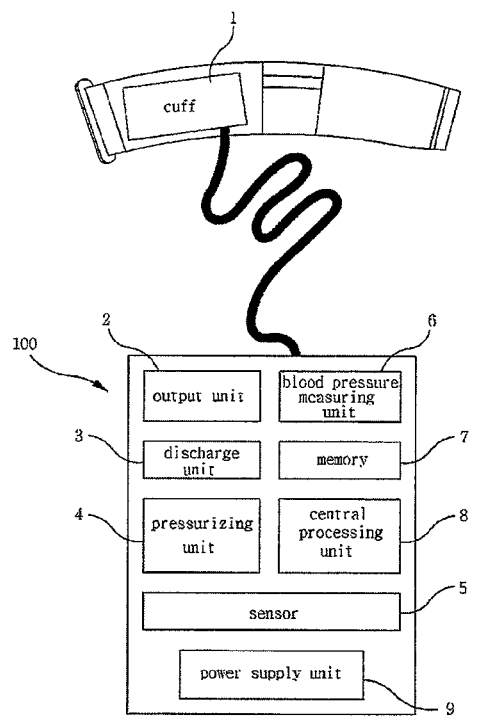
FIG. 3 is a block diagram showing the apparatus of measuring a blood pressure according to the present invention.

As shown in FIG. 3, the apparatus 100 of measuring a blood pressure according to the present invention, which can measure the postures or the activity states of an examinee, has a structure similar to that of a typical blood pressure gauge capable of monitoring the blood pressure of the examinee for about 24 hours. However, in the apparatus 100 of measuring the blood pressure according to the present invention, a sensor is not provided to a cuff to measure the blood pressure of the examinee, but provided in a body of a gauge attached to a human body of the examinee.

Figure 4:
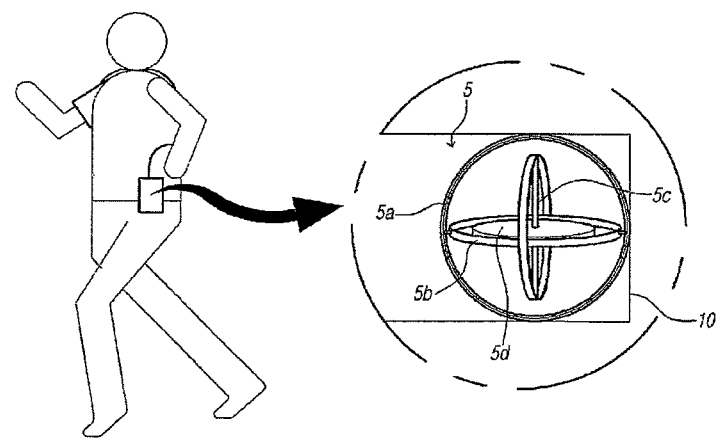
FIG. 4 is a view showing an example of the structure of a sensor installed in a body of a blood pressure gauge of the apparatus of measuring a blood pressure according to the present invention to detect the movement, position, or direction of the blood pressure gauge.

Referring to FIGS. 3 and 4, the information about the posture or the activity state of the examinee is detected by a sensor 5 installed in a body 10. Simultaneously, the blood pressure of the examinee is measured, so that the information about the posture or the activity state of the examinee and the information about the blood pressure of the examinee are recorded at the same time. Therefore, the posture of the examinee can be determined when the blood pressure of the examinee is measured. On the assumption that measurement results such as the systolic pressure of 130 mmHg, the diastolic pressure of 70 mmHg, and a pulse rate of 76 are acquired, it can be determined whether the measurement results are acquired when the examinee lies down or stands up.

A conventional blood pressure gauge capable of monitoring the blood pressure of the examinee for 24 hours represents different measurement results of the blood pressure according to the posture and activities of the examinee, for example, walking, sitting, and running. In addition, the difference of the measurement results is variously represented according to the body characteristics of persons. For example, a person having the systolic pressure of 125 mmHg and the diastolic pressure of 85 mmHg in a stable state represents the systolic pressure of 100 mmHg and the diastolic pressure of 70 mmHg in a lying state, and represents the systolic pressure of 155 mmHg and the diastolic pressure of 93 mmHg in a running state.

In order to exactly check the blood pressure of an examinee representing the great deviation in the blood pressure according to the postures, as shown in FIG. 3, an apparatus 100 of measuring the blood pressure includes a cuff 1 attached to an arm of the examinee, a pressurizing unit 4 to pressurize the cuff 1 for the purpose of measuring the blood pressure of the examinee, a discharge unit 3 to release the pressure of the cuff 1 for the purpose of measuring the blood pressure of the examinee, a blood pressure measuring unit 6 to measure the blood pressure of the examinee, the sensor 5 installed in the body 10 to detect the posture or the activity state of the examinee, a central processing unit 8 receiving the information about the blood pressure and the information about the posture or the activity of the examinee measured by the blood pressure measuring unit 6 and the sensor 5, respectively, to perform a comparison operation with respect the two pieces of information according to a preset program, a memory 7 storing resulted information after the information has been compared in the central processing unit 8, an output unit 2 outputting the information about the posture or the activity state of the examinee measured in the sensor 5 and the information about the blood pressure of the examinee measured in the blood pressure measuring unit 6, and a power supply unit 9 supplying power to each component.

The pressurizing unit 4 has a plurality of driving modes such that the speed to pressurize the cuff 1 is applied in a plurality of steps when the blood pressure of the examinee is measured. According to the invention, the pressurizing unit 4 has two driving modes including first and second driving modes. In the first driving mode (normal driving mode), the speed to pressurize the cuff 1 is more normally applied as compared with the second driving mode (sleep driving mode).

As shown in FIG. 4, the sensor 5 installed in the body 10 of a blood pressure gauge according to the present invention includes a gyroscope, which is generally known to those skilled in the art, including a frame 5a, a gimbal 5b, a rotational shaft 5c, and a rotor 5d, so that the central processing unit 8 can receive detection signals related to the direction, position, and movement state of the body 10 of the blood pressure gauge.

If the detection signals for the direction, position, and activity of the body 10 of the blood pressure gauge are input into the central processing unit 8, the central processing unit 8 specifies predetermined signal bands based on the type of the detection signals supplied at predetermined time intervals (e.g., the time interval, such as one minute or three minutes preset by a program), so that a plurality of signal band groups are specified corresponding to the time intervals.

Figures 5, 6:
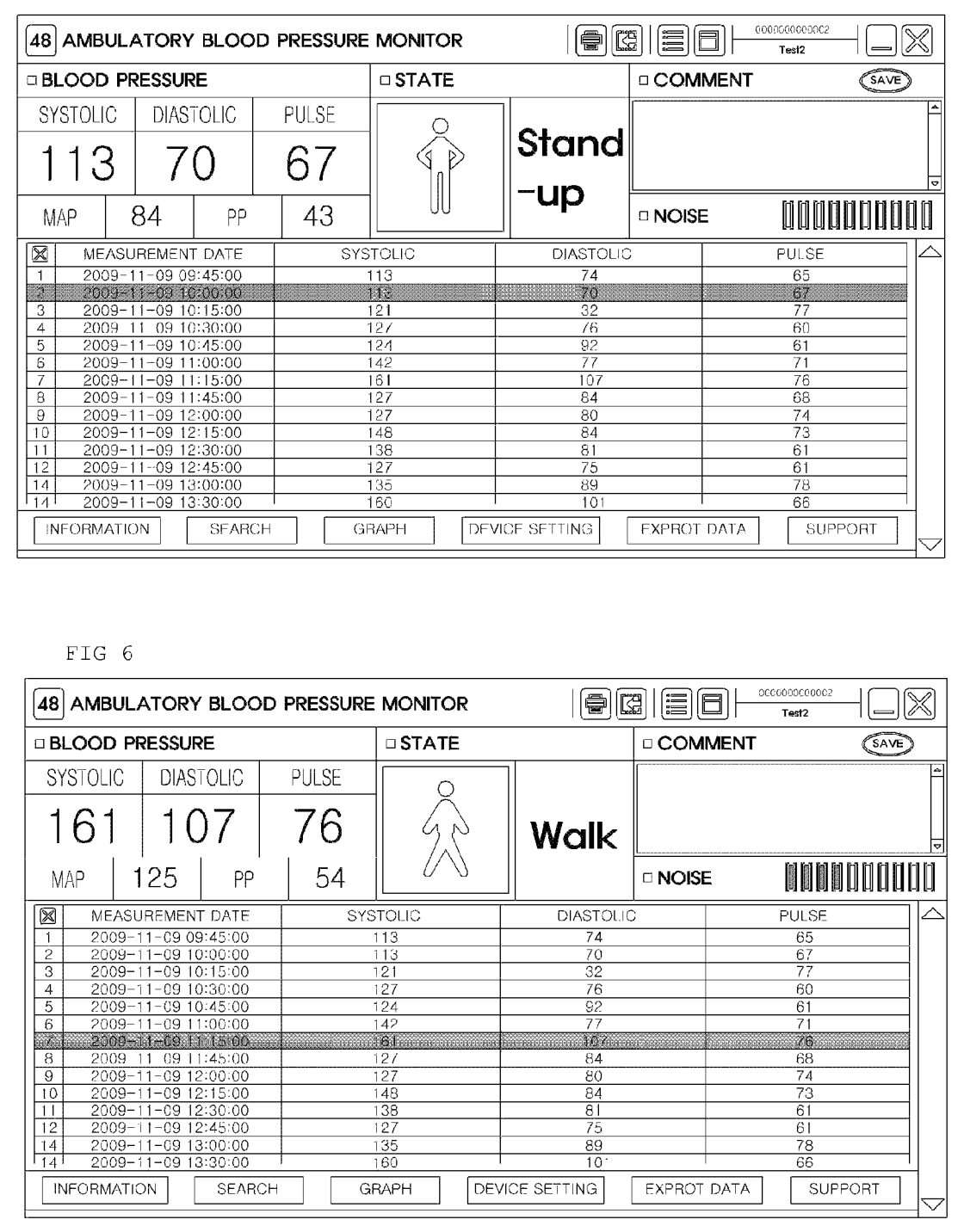

For example, in a predetermined time interval, if signals, which represent that the body 10 of the blood pressure gauge is in an upright state without moving, are continuously received corresponding to 80% based on the total signals, as shown in FIG. 5, it is determined that the blood pressure of the examinee is measured as the examinee is in a stand-up state, and the information about the blood pressure of the examine may be output or stored.

In addition, in a predetermined time interval, if signals, which represent that the body 10 of the blood pressure gauge is in an upright position while moving in some degree, are continuously received corresponding to 80% based on total signals, as shown in FIG. 6, it is determined that the blood pressure of the examinee is measured when the examinee is in a walking state, and the information about the blood pressure of the examine may be output or stored.

Figure 9:
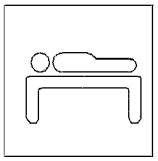
FIG. 9 is a view showing output data related to the blood pressure of the examinee measured by using the apparatus of measuring a blood pressure according to the present invention when the examinee lies down.

In addition, in a predetermined time interval, signals, which represent that the body 10 of the blood pressure gauge is in a flat position without moving for a predetermined time interval, are continuously received corresponding to 80% based on total signals, as shown in FIG. 9, it is determined that the blood pressure of the examinee is measured when the examinee lies down, and the information about the blood pressure of the examine may be output or stored.

Figure 10:
FIG. 10 is a view showing output data related to the blood pressure of the examinee measured by using the apparatus of measuring a blood pressure according to the present invention when the examinee is tossing and turning in the laying state.

In the same manner, in a predetermined time interval, if signals, which represent that the body 10 of the blood pressure gauge is in a flat position and moves in some degree, are continuously received corresponding to 80% based on total signals, as shown in FIG. 10, it is determined that the blood pressure of the examinee is measured when the examinee tosses and turns, and the information about the blood pressure of the examine is output or stored.

The information about the blood pressure may be directly output through the screen of the output unit 2, or may be displayed through an additional monitor connected to the output unit 2.

Meanwhile, in the process of periodically measuring the blood pressure of the examinee as time elapse, the mode of the pressurizing unit 4 of the apparatus 100 of measuring the blood pressure according to the present invention is changed into the first driving mode or the second driving mode according to the posture states of the examinee.

For example, when the blood pressure of the examinee is measured in a state where the examinee does not lie down to keep equilibrium and does not asleep, the cuff 1 can be rapidly pressurized. In this case, the central processing process unit 8 performs a comparison operation between blood pressure measurement timing and the signal band received by the sensor 5 and controls the cuff 1 such that the cuff 1 is pressurized at the first driving mode which is a normal driving mode.

In contrast, when the blood pressure of the examinee is measured at a state where the examinee leis down to keep equilibrium, sleeps deeply, or tosses and turns in a sleeping state, the cuff 1 needs to be slowly pressurized such that the examinee cannot recognize the measurement of the blood pressure in the above state. Accordingly, the central processing process unit 8 performs a comparison operation between blood pressure measurement timing and the signal band received by the sensor 5 and controls the cuff 1 such that the cuff 1 is pressurized at the second driving mode which is a sleep driving mode.

Figure 11:
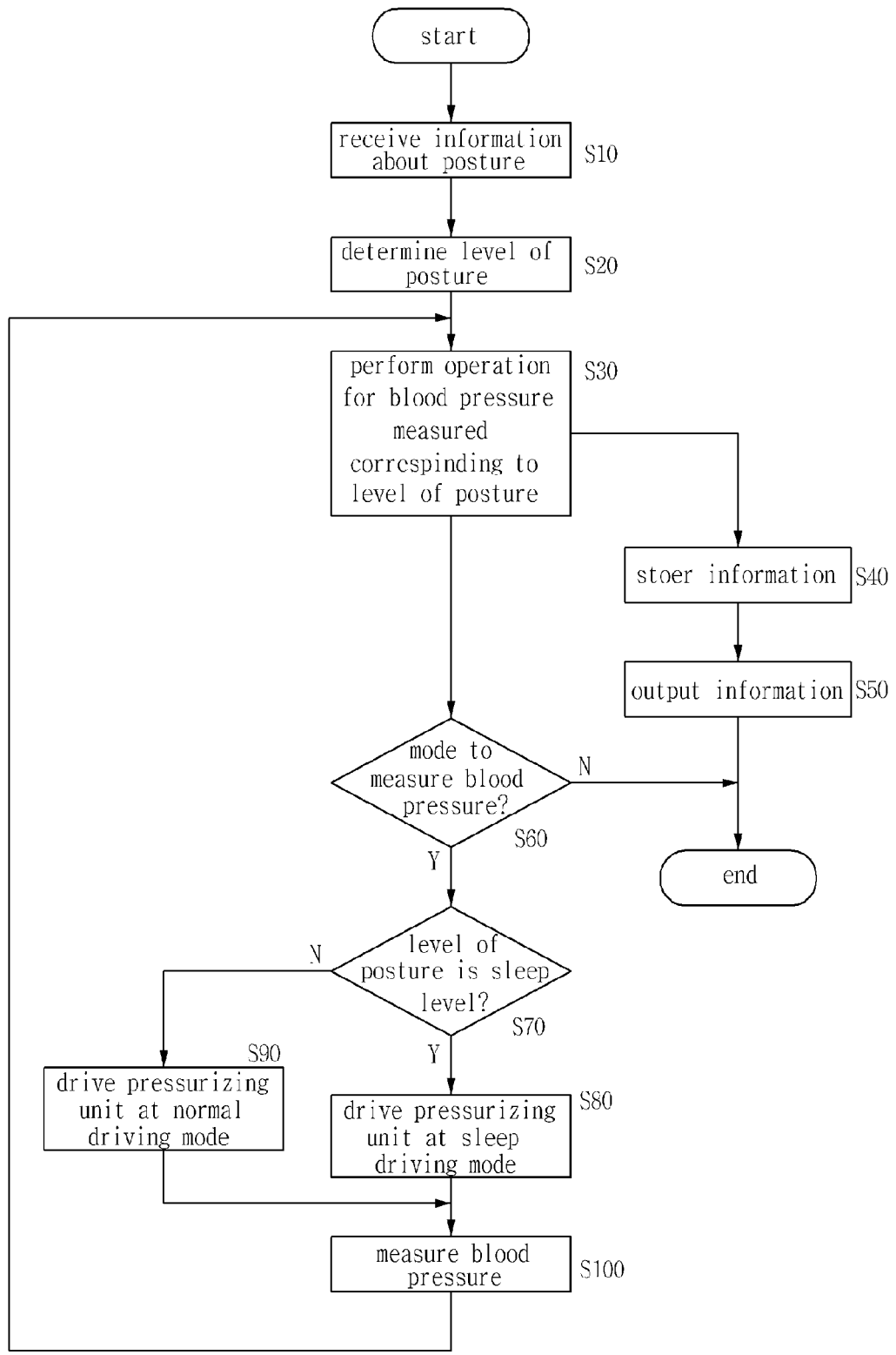
FIG. 11 is a flowchart showing the operating procedure of the apparatus of measuring a blood pressure according to the present invention.

When the apparatus 100 of measuring the blood pressure of the present invention manually specifies one of the first and second driving modes and drives the pressurizing unit 4, the apparatus 100 of measuring the blood pressure can drive the pressurizing unit 4 at the same driving mode regardless of the posture states of the examinee whenever the blood pressure of the examinee is measured Hereinafter, the operating procedure of the apparatus of measuring the blood pressure having the above structure according to the present invention will be described with reference to FIG. 11.

First, the central processing unit 8 receives information about the posture of the examinee in real time through the sensor 5 installed in the body 10 (step S10).

If the information about the posture state of the examinee is received, the central processing unit 8 specifies signal bands based on the type of signals related to the posture of the examinee supplied at predetermined time intervals, so that a plurality of signal band groups are classified corresponding to the time intervals, thereby determining the level for the posture state of the examinee (step S20).

Then, if the blood pressure of the examinee is first measured in a predetermined time interval, the central processing unit 8 performs a predetermined operation for the information about the blood pressure together with the level for the posture state of the examinee corresponding to the time interval (step S30) to store the measured information about the blood pressure in the memory 7 (step S40) or output the information about the blood pressure through the output unit 2 (step S50).

Then, the central processing unit 8 determines if a blood pressure measuring mode is maintained at a predetermined time interval after the first blood pressure has been measured (step S60). If the blood pressure measuring mode is maintained in step S60, the central processing unit 8 determines if the posture state of the examinee corresponds to a sleep level at a second blood pressure measuring timing (step S70). If the blood pressure measuring mode is released, the measurement of the blood pressure is terminated.

If the level for the posture state of the examinee is identical to the sleep level in step S70, the pressurizing unit 4 is driven at the sleep driving mode, that is, the second driving mode (step S80) and pressurizes the cuff 1, such that the second blood pressure of the examinee is measured (step S100). If the posture state of the examinee is not identical to the sleep level, the pressurizing unit 4 is driven at the normal driving mode, that is, the first driving mode (step S90) and pressurizes the cuff 1 such that the second blood pressure of the examinee is measured (step S100).

Although the second driving mode (the sleep driving mode) is activated when a signal representing that the examinee lies down for a predetermined time or tosses and turns in a lying state is detected, the setting of the driving mode may be changed according to the setting of a program.

Meanwhile, the blood pressure that has been measured in step S100 is subject to a comparison operation by the central processing unit 8 in step S30. Then, the information 10 about the blood pressure is stored with the information about the posture state of the examinee or output.

Step S30 to step S100 are repeated from the third measurement of the blood pressure until the measurement of the blood pressure has been finished.

Although the present invention has been described with reference to a number of illustrative embodiments thereof, it should be understood that numerous other modifications and embodiments can be devised by those skilled in the art that will fall within the scope of accompanying claims and the objects of the present invention.

INDUSTRIAL APPLICABILITY

The present invention is applicable to an apparatus of measuring a blood pressure.

The invention claimed is:
1. An apparatus of measuring a blood pressure of an examinee while detecting a body activity of the examinee, the apparatus comprising:
a cuff;
a pressurizing unit to pressurize the cuff;
a discharge unit to release a pressure of the cuff;
a blood pressure measuring unit to measure the blood pressure by pressurizing the cuff;
a central processing unit to perform a predetermined operation with respect to the measured blood pressure;
a memory to store information about the measured blood pressure that is obtained from the predetermined operation;
a data output unit to output the information about the measured blood pressure stored in the central processing unit or the memory; and
a sensor installed in a body of a blood pressure gauge to detect movement, a position, or a direction of the blood pressure gauge,
wherein the central processing unit is configured to generate blood pressure data by performing the operation based on the measured blood pressure using the blood pressure measuring unit, to determine whether the body activity of the examinee is in a first activity type or a second activity type based on the detected movement, position, or the direction of the blood pressure gauge, and to control the cuff to be in a first driving mode or a second driving mode, in response to determining that the body activity is in the first activity type or the second activity type, the cuff being pressurized at a different rate in the first driving mode from in the second driving mode,
wherein the first activity type is an activity type where the examinee is in motion, and the second activity type is an activity type where the examinee is idle, and
wherein the central processing unit is further configured to control the cuff to be pressurized at a more rapid rate in the first pressure mode in response to determining that the body activity is in the first activity mode.
2. The apparatus of claim 1, wherein the pressurizing unit has the first and second driving modes for pressurizing the cuff, and
wherein the central processing unit classifies signals, which represent the movement, the position, or the direction of the blood pressure gauge detected by the sensor, into a plurality of groups, and selectively per- forms the first driving mode or the second driving mode according to signal bands classified into the plurality of groups.

3. The apparatus of claim 2, wherein the cuff is pressurized more rapidly in the first driving mode than in the second driving mode, and the central processing unit performs the second driving mode if the blood pressure is measured in two signal bands selected from the plurality of groups of signal bands, and performs the first driving mode if the blood pressure is measured in remaining signal bands.

4. A method of measuring a blood pressure of an examinee while detecting a body activity of the examinee, the method comprising:

measuring a first blood pressure of the examinee by pressurizing a cuff with one of first and second driving modes of a pressurizing unit;

receiving information about movement, a position, or a direction of a blood pressure gauge, which is detected by a sensor installed in a body of the blood pressure gauge, in real time and classifying the body activity of the examinee, based on the information about the movement, the position, or the direction of the blood pressure gauge, into a plurality of activity types for the examinee by a central processing unit;

outputting the information about the movement, the position, or the direction of the blood pressure gauge and information about the measured first blood pressure through an output unit corresponding to time periods at which the first blood pressure of the examinee is measured, or storing the information about the movement, the position, or the direction of the blood pressure gauge and the information about the measured first blood pressure in a memory by the central processing unit;

determining, by the central processing unit, whether the body activity of the examinee is in a first activity type or a second activity type among the plurality of activity types, based on the information about the movement, the position, or the direction of the blood pressure gauge;

measuring a second blood pressure of the examinee by selectively driving the cuff in a first driving mode or a second driving mode, in response to determining that the body activity of the examinee is in the first activity type or the second activity type, the cuff being pressurized at a different rate in the first driving mode from in the second driving mode; and repeating the receiving information step, the outputting step, and the measuring the second blood pressure step, wherein the first activity type is an activity type where the examinee is in motion, and the second activity type is an activity type where the examinee is idle, and wherein the cuff is pressurized at a more rapid rate in the first pressure mode in response to determining that the body activity is in the first activity mode.

5. The method of claim 4, wherein the information about the movement, the position, or the direction of the blood pressure gauge detected by the sensor is represented as signals that are categorized into a plurality of groups, and the first driving mode or the second driving mode is performed according to signal bands classified into the plurality of groups, and wherein the cuff is pressurized more rapidly in the first driving mode than in the second driving mode, and the second driving mode is performed if the blood pressure is measured in two signal bands selected from the plurality of grouped signal bands, and the first driving mode is performed if the blood pressure is measured in remaining signal bands.

6. The apparatus of claim 1, wherein the central processing unit is further configured to control the cuff to be pressurized at a slower rate in the second pressure mode in response to determining that the body activity is in the second activity mode.

7. The method of claim 4, wherein the cuff is pressurized at a slower rate in the second pressure mode in response to determining that the body activity is in the second activity mode.

\* \* \* \* \*